United States Patent [19]

Imai et al.

[11] Patent Number: 5,166,117

[45] Date of Patent: Nov. 24, 1992

[54] POLYMERIZATION INITIATOR COMPOSITION CONTROLLING POLYMERIZATION AT INTERFACE AND CURABLE COMPOSITION CONTAINING SAME

[75] Inventors: Yoji Imai, Chiba; Yoshinori Kadoma, Tokyo; Toru Kawashima, Ashigarakami, all of Japan

[73] Assignee: Terumo Kabushiki Kaisha, Tokyo, Japan

[21] Appl. No.: 758,555

[22] Filed: Sep. 12, 1991

[30] Foreign Application Priority Data

Sep. 14, 1990 [JP] Japan .................................. 2-245431

[51] Int. Cl.⁵ ........................ B01J 31/00; C08F 4/00; C07D 239/02
[52] U.S. Cl. ................................... 502/169; 526/204; 544/299
[58] Field of Search ............... 526/204, 205; 544/299; 502/169

[56] References Cited

FOREIGN PATENT DOCUMENTS 59-28569 7/1984 Japan .

OTHER PUBLICATIONS

"Dental Materials and Instruments" vol. 8, Special Issue No. 14, pp. 89-90 (1989).

Primary Examiner—Joseph L. Schofer
Assistant Examiner—Wu C. Cheng
Attorney, Agent, or Firm—Burns, Doane, Swecker & Mathis

[57] ABSTRACT

A polymerization initiator composition controlling polymerization at interface, comprising a (thio)barbituric acid compound represented by the general formula I:

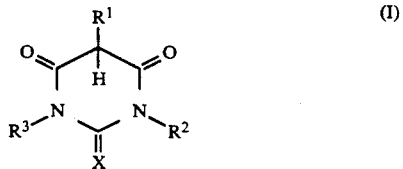

wherein $R^1$ is an alkyl group of 1 to 3 carbon atoms, $R^2$ and $R^3$ are independently hydrogen atom or an alkyl group of 1 to 3 carbon atoms, and X is oxygen atom or sulfur atom, and (a) a metal halide represented by the general formula, $MY_n$ wherein M is Cu or Fe, Y is halogen atom, and n is an integer of 2 when M is Cu or an integer of 3 when M is Fe, or (b) a halogen ion-forming compound and $M^m$-forming compound wherein M is Cu or Fe and m is 2+ when M is Cu or 3+ when M is Fe, and a curable composition comprising the (thio)barbituric acid and radically polymerizable monomer.

5 Claims, No Drawings

POLYMERIZATION INITIATOR COMPOSITION CONTROLLING POLYMERIZATION AT INTERFACE AND CURABLE COMPOSITION CONTAINING SAME

BACKGROUND OF THE INVENTION

1. Field of the Invention

This invention relates to a polymerization initiator composition which controls polymerization at interface and a curable composition which contains it.

2. Description of the Prior Art

In the dental treatment, adhesion is required between dentins and polymeric, metallic, and other materials. Various adhesives have been proposed for the purpose of this adhesion. The idea underlying these adhesives comprises making effective use of a polymerizable monomer exhibiting affinity for dentins. Compounds possessing a carboxyl group include 4-methacryloyloxyethoxy carbonyl phthalic acid and anhydride thereof and 10-methacryloyloxy decyl malonic acid and compounds possessing a phosphoric acid group include 10-methacryloyloxy decyl dihydrodiene phosphate, for example. The polymerizable monomers which are mixable with such compounds include methyl methacrylate, bisphenol A-glycidyl methacrylate adduct, and triethylene glycol dimethacrylate, for example.

As respects polymerization initiators for curing these polymerizable monomers, those which effect the curing by virtue of a free radical generated in a chemical reaction performed at room temperature (at about 25° C.) include benzoyl peroxide/amine type compounds, compounds of the same type additionally incorporating sulfinates therein, and tributyl boranes and oxides and those which attain the curing by dint of a free radical generated in a photoreaction include camphorquinone/N,N-dimethylaminoethyl methacrylate and other type of amines, for example.

The conventional technique has placed emphasis on adhesive monomers. Even when a monomer capable of promoting adhesion is present on the interface of a dentin, no strong adhesive (bonding) strength is obtained unless the curing of this monomer proceeds inwardly from the interface thereof. Unless the polymerization initiator to be used is specially devised, it is only natural that owing to the shrinkage which occurs in consequence of the polymerization of the monomer, the interface should sustain strain, constitute itself the weakest part throughout the entire thickness of the polymer, and tend to fracture. In accordance with the conventional technique, therefore, even the use of the monomer for promoting adhesion fails to produce sufficient adhesive strength unless an oxide of tributyl borane is used in combination with ferric chloride.

Indeed, the oxide of tributyl borane plus the iron chloride is effective in the polymerization which proceeds inwardly from the dentinal interface. The adhesive agent which uses the oxide of tributyl borane, however, suffers the inevitability of using the oxide of tributyl borane in a proportion of 10% or more based on the amount of the monomer, retarding the curing, limiting the polymerizing monomer virtually to methyl methacrylate alone, and prohibiting use of dimethacrylates.

A photopolymerizing dental material made of a vinyl monomer, camphor quinone, and a 5-alkylbarbituric acid has been known in the art (JP-B- 59-28,569(1994)). Since this material necessitates irradiation with light, it is unfit for adhesion to the interface of a dentin.

We formerly found the fact that 5-n-butyl barbituric acid and cupric chloride are allowed polymerization at interface when they are combined with methyl methacrylate ("Dental Materials and Instruments," Vol. 8, Special Issue No. 14, pp. 89-90 (1989)).

Since 5-n-butyl barbituric acid imparts no sufficient adhesive strength and exhibits poor solubility to the monomers, however, the combination using it has the disadvantage that it must be consumed in a large amount and fails to cure quickly.

An object of this invention, therefore, is to provide a novel polymerization initiator composition controlling polymerization at interface and a curable composition containing it.

Another object of this invention is to solve the problems attendant upon the conventional techniques as described above by devising means of initiating the curing from the interface rich in moisture and consequently provide a polymerization initiator which exhibits outstanding adhesive strength to the dentins of teeth rich in moisture, necessitates only a small consumption, cures quickly, and allows use of a wide variety of monomers as polymerizable monomers besides MMA and also provide a composition containing the polymerization initiator.

SUMMARY OF THE INVENTION

These objects are accomplished by a polymerization initiator composition controlling polymerization at interface, comprising a (thio)barbituric acid compound represented by the general formula I:

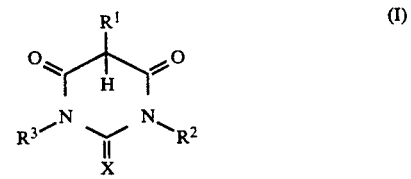

wherein $R^1$ is an alkyl group of 1 to 3 carbon atoms $R^2$ and $R^3$ are independently hydrogen atom or an alkyl group of 1 to 3 carbon atoms, and X is oxygen atom or sulfur atom, and (a) a metal halide represented by the general formula, $MY_n$ wherein M is Cu or Fe, Y is halogen atom, and n is an integer of 2 where M is Cu or an integer of 3 where M is Fe, or (b) a halogen ion-forming compound and a $M^m$-forming compound wherein M is Cu or Fe and m is 2+ when M is Cu or 3+ when M is Fe.

These objects are further accomplished by a curable composition, comprising a (thio)barbituric acid compound represented by the general formula I mentioned above, (a) a metal halide represented by the general formula, $MY_n$ wherein M, Y, and n have the same meanings as defined above, or (b) a halogen ion-forming compound and a $M^m$-forming compound wherein M and m have the same meanings as defined above, and a radically polymerizable monomer.

This invention discloses a curable composition comprising 100 parts by weight of a radically polymerizable monomer as a basis, 0.1 to 10 parts by weight of the (thio)barbituric acid compound mentioned above, and 0.0001 to 0.5 part by weight of (a) a metal halide represented by the general formula, $MY_n$ wherein M, Y, and n have the same meanings as defined above, or (b) a halogen ion-forming compound and a $M^m$-forming compound wherein M and m have the same meanings as defined above. This invention further discloses a curable composition to be used in the adhesion to dentins.

This invention is directed to a polymerization initiator composition curbing polymerization a interface which comprises a (thio)barbituric acid compound represented by the general formula I and (a) a cupric halide or a ferric halide or (b) a halogen ion-forming compound and a cupric or ferric ion-forming compound. The us of this polymerization initiator composition, therefore, enables a monomer to be quickly cured at room temperature with a small consumption of the composition and to be joined with high adhesive strength to dentins.

The curing composition of the present invention comprises the polymerization initiator mentioned above and a radically polymerizable monomer. It is, therefore, enabled not only to adhere to a dentin hydrated at room temperature but also to induce adhesion to a hydrated interface and polymerization and graft polymerization on the hydrated surface of such a material as film or fiber.

EXPLANATION OF THE PREFERRED EMBODIMENT

For the purpose of initiating a polymerization from the interface of a dentin rich in moisture, an idea of resorting to the combination of a redox type initiator with a substance easily incorporated in the interface may be conceived. As the redox type components which are easily incorporated in the interface, copper chloride, iron chloride, etc. may be cited. A study continued in search of various components useful for combination with these components has demonstrated that (thio)barbituric acid compounds are best suited for the combination.

The redox type components which are effectively usable in this invention for incorporation in the dentins include cupric halides such as cupric chloride and cupric bromide and ferric halides such as ferric chloride and ferric bromide. Among other redox type components cited above, cupric halides prove to be particularly desirable. The combinations of halogen ion-forming compounds with cupric or ferric ion-forming compounds, preferably cupric ion-forming compounds, can be used as redox type components. The halogen ion-forming compounds include hydrochlorides of amines such as methyl amine, dimethyl amine, trimethyl amine, ethyl amine, diethyl amine, triethyl amine, n-propyl amine, isopropyl amine, butyl amines, pyridines, hydrohalides such as hydrobromic acid salts, methacryloyl choline chloride, and acryloyl choline chloride, for example. The cupric and ferric ion-forming compounds include organic acid salts such as copper acetate, copper propionate, copper succinate, copper acrylate, copper methacrylate, copper maleate copper fumarate, iron acetate, propionates, iron succinate, iron acrylate, iron methacrylate, iron maleate, and iron fumarate, for example.

The (thio)barbituric acid compounds which are usable herein include 1,3,5-trimethyl (thio)bariburic acid, 1,3,5-triethyl (thio)barbituric acid, 1,3-dimethyl-5-ethyl (thio)barbituric acid, 1-methyl-3-propyl-5-ethyl (thio)-barbituric acid, 1-ethyl-3-propyl-5-methyl (thio)barbituric acid, 1,5-dimethyl (thio)barbituric acid, 1-methyl-5-ethyl (thio)barbituric acid, 5-methyl (thio)barbituric acid, 5-ethyl (thio)barbituric acid, and 5-propyl (thio)barbituric acid, for example.

The amount of (a) a cupric halide or a ferric halide or (b) a halogen ion-forming compound and a cupric or ferric ion-forming compound to be used is preferable to be in the range of from 0.001 to 1 part by weight, preferably from 0.01 to 0.5 part by weight, based on 100 parts by weight of the (thio)barbituric acid compound.

The curing composition according with the present invention comprises a (thio)barbituric acid compound represented by the general formula I mentioned above, (a) a cupric halide or a ferric halide or (b) a halogen ion-forming compound and a cupric or ferric ion-forming compound, and a radically polymerizable monomer.

The radically polymerizable monomers which are usable herein include alkyl (meth)acrylates such as methyl (meth)acrylates, ethyl (meth)acrylates, isopropyl (meth)acrylates, and butyl (meth)acrylates, (meth)acrylic esters possessing a carboxyl group or a phosphoric acid group in the side chains, diacrylic or dimethacrylic esters of diols such as ethylene glycol di(meth)acrylates, diethylene glycol di(meth)acrylates, triethylene glycol di(meth)acrylates, butylene glycol di(meth)acrylates, and hexane diol di(meth)acrylates, trimethylol propane di(meth)acrylates, and bis-phenol A-glycidyl methacrylate adducts, for example.

The radically polymerizable monomer may be a complete monomer or a syrupy substance partially containing a polymer.

Based on the amount of the radically polymerizable monomer taken as 100 parts by weight, the amount of the (thio)barbituric acid compound is in the range of from 0.1 to 10 parts by weight, preferably from 0.5 to 5 parts by weight, and the amount of (a) the cupric halide or ferric halide or (b) the halogen ion-forming compound and the cupric ion- or ferric ion-forming compound is in the range of 0.0001 to 0.5 part by weight, preferably from 0.001 to 0.1 part by weight.

For the purpose of improving the solubility of the polymerization initiator or enhancing the wettability of the monomer in the interface rich in moisture, the radically polymeriable monomer may additionally incorporate therein a water-soluble monomer in an amount in the range of from 0.5 to 50% by weight, preferably from 1 to 10% by weight, based on the amount of the polymerizable monomer. The water-soluble monomers which are usable for this purpose include 2-hydroxyethyl (meth)acrylates, N-(meth)acryloyloxyethyl pyrrolidones, 2,3-dihydroxypropyl (meth)acrylates, N-vinyl pyrrolidone, dimethylaminoethyl (meth)acrylates, and diacetone (meth)acrylamides, for example. Further, the incorporation into the curable composition of a water-soluble organic solvent such as ethanol, isopropanol, acetone, or tetrahydrofuran in an amount in the range of from 0.1 to 50% by weight, preferably from 1 to 10% by weight, based on the amount of the radically polymeriable monomer may be effected as occasion demands. The curable composition according with the present invention may further incorporate therein other polymer, a filler, a stabilizer, etc.

The adhesion to the dentin of a tooth is effected by a method which comprises pretreating the dentin with an aqueous citric acid solution containing cupric chloride or ferric chloride and washing the pretreated dentin with water or pretreating the dentin with citric acid, phosphoric acid, or ethylene diaminetetraacetic acid and washing the pretreated dentin with water, coating the cleaned dentin with an aqueous 0.001 to 0.1% cupric chloride solution, and applying to the coated dentin a monomer composition containing cupric or ferric chloide and a (thio)barbituric acid compound. The adhesion to an enamel may be prepared solely by etching with an acid.

The use of the polymerization initiator composition according with the present invention not only allows adhesion to a hydrated dentin at room temperature but also induces adhesion to an interface in a hydrated state and polymerization or graft polymerization on the surface of a hydrated material such as film or fiber.

Now, the present invention will be described more specifically below with reference to referential examples and working examples.

Method for Determination of Adhesive Strength

A bovine anterior tooth was cut with a diamond cutter and the pulpal side dentin surfaces of the cut tooth was used as a test piece for adhesion. The test piece was treated for 30 seconds with an aqueous 10% by weight citric acid solution containing 3% by weight of cupric chloride, washed with water, and dried. A plastic adhesive tape containing a hole 5 mm in diameter was applied to the cleaned test piece to define a surface area for adhesion. A sample curing composition was applied to the surface area and an acryl bar was fixed to the applied layer of the sample. The acryl bar as stuck to the test piece was left standing at room temperature for 30 minutes, further stored in distilled water at 37° C. for 24 hours, and thereafter subjected to a tensile test to determine the adhesive strength of the sample. The average of the results found for a total of five test pieces was reported.

EXAMPLE 1

A liquid component was obtained by dissolving 0.003% by weight of cupric chloride in methyl methacrylate (MMA) containing 2% by weight of 2-hydroxyethyl methacrylate and a powder component was obtained by mixing a polymethyl methacrylate (PMMA) type powder with 2% by weight of 1,3,5-trimethyl-2-thiobarbituric acid. When the powder and the liquid were mixed in a ratio of 1:1, the resultant mixture was cured in 9.4 minutes. When dentinal pieces were adhered with this mixture, the adhesive strength was 13.9 MPa.

EXAMPLES 2 to 6

The procedure of Example 1 was repeated, except that the concentrations of raw materials and the kind of barbituric acid compound were varied as shown in Table 1.

TABLE 1

| Example | Cupric chloride (% by weight) | Barbituric acid | Curing time (min.) | Adhesive strength (MP a) |
|---|---|---|---|---|
| 2 | 0.015 | 2% 1,3,5-Trimethyl thiobarbituric acid | 4.5 | 10.5 |
| 3 | 0.006 | 2% 1,3,5-Trimethyl barbituric acid | 6.0 | 12.2 |
| 4 | 0.008 | 2% 1,5-Dimethyl barbituric acid | 5.3 | 11.5 |
| 5 | 0.003 | 4% 5-n-Propyl barbituric acid | 6.0 | 10.8 |
| 6 | 0.005 | 4% 5-Ethyl barbituric acid | 5.3 | 10.0 |

EXAMPLE 7

The procedure of Example 5 was repeated, except that ethylene glycol dimethacrylate was further added in 1% to methyl methacrylate. The curing time was 5.8 minutes and the adhesive strength was 14 MPa.

EXAMPLE 8

The procedure of Example 1 was repeated, except that ethanol was used in the place of 2-hydroxyethyl methacrylate. The curing time was 9 minutes and the adhesive strength was 12.7 MPa.

EXAMPLE 9

The procedure of Example 1 was repeated, except that a liquid component was obtained by adding 5% by weight of 2hydroxyethyl methacrylate, 0.01% by weight of copper methacrylate, and 0.05% by weight of methacryloyl choline chloride to methyl methacrylate and 1,3,5-trimethyl barbituric acid was used in the place of thio-barbituric acid. The curing time was 3.0 minutes and the adhesive strength was 9.1 MPa.

EXAMPLE 10

The procedure of Example 1 was repeated, except that 0.03% by weight of ferric chloride was used in the place of 0.003% by weight of cupric chloride. The curing time was 10.5 minutes and the adhesive strength was 12.8 MPa.

EXAMPLE 11

The procedure of Example 1 was repeated, except that a liquid component incorporated 0.01% by weight of iron acetylacetonate and 0.08% by weight of n-propyl amine hydrochloride in the place of 0.003% by weight of cupric chloride. The curing time was 6.5 minutes and the adhesive strength was 9.5 MPa.

EXAMPLE 12

In the determination of adhesive force in the procedure of Example 1, when the dentin was treated with an aqueous 10% citric acid solution in the place of the aqueous 10% citric acid solution containing 3% cupric chloride, washed with water, dried, coated with an aqueous 0.01% cupric chloride solution, and dried, and the acryl rod was adhered to the cleaned dentin with the curing composition of Example 1, the adhesive strength was 13.2 MPa.

Control 1

When a commercially available adhesive agent "Super Bond" produced by mixing a polymethyl methacrylate type powder with a liquid component resulting from addition of 9.8% by weight of tributyl borane oxide to methyl methacrylate containing 5% by weight of 4-methacryloyloxyethoxycarbonyl phthalic anhydride was used, the curing time was 11.0 minutes, and the adhesive strength was 11.9 MPa.

What is claimed is:

1. A polymerization initiator composition controlling polymerization at interface, comprising a (thio)barbituric acid compound represented by the general formula I:

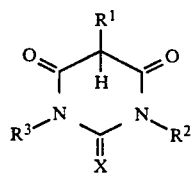

wherein $R^1$ is an alkyl group of 1 to 3 carbon atoms, $R^2$ and $R^3$ are independently hydrogen atom or an alkyl group of 1 to 3 carbon atoms, and X is oxygen atom or sulfur atom, and (a) a metal halide represented by the general formula, $MY_n$ wherein M is Cu or Fe, Y is halogen atom, and n is an integer of 2 when M is Cu or an integer of 3 when M is Fe, or (b) a halogen ion-forming compound and $M^m$-forming compound wherein M is Cu or Fe and m is 2+ when M is Cu or 3+ when M is Fe.

2. A composition according to claim 1, wherein the amount of (a) said metal halide or (b) said halogen ion-forming compound and said $M^m$-forming compound is in a range of from 0.001 to 1 part by weight, based on 100 parts by weight of said (thio)barbituric acid compound.

3. A composition according to claim 1, wherein Y in said general formula I is chlorine or bromine.

4. A composition according to claim 3, wherein the amount of (a) said metal halide or (b) said halogen ion-forming compound and $M^m$-forming compound is in a range of from 0.01 to 0.5 part by weight, based on 100 parts by weight of said (thio)barbituric acid compound.

5. A composition according to claim 1, wherein said halogen ion-forming compound is a hydrogen halogenic acid of an amine or (meth)acryloyl choline chloride and said $M^m$-forming compound is a copper or iron salt of an organic acid.

* * * * *